US00PP08150P

United States Patent [19]

van der Knapp

[11] Patent Number: Plant 8,150

[45] Date of Patent: Feb. 16, 1993

[54] CHRYSANTHEMUM PLANT — TOUCH CULTIVAR

[75] Inventor: Jacques C. M. van der Knapp, De Lier, Netherlands

[73] Assignee: Fides Beheer B.V., De Lier, Netherlands

[21] Appl. No.: 720,666

[22] Filed: Jun. 25, 1991

[51] Int. Cl.[5] ..... A01H 5/00

[52] U.S. Cl. ..... Plt./82.2

[58] Field of Search ..... Plt./74.1, 82.2, 82.3, Plt./76, 78

[56] References Cited

U.S. PATENT DOCUMENTS

P.P. 6,299 9/1988 van der Knaap ..... Plt. 82.2

P.P. 6,300 9/1988 van der Knaap ..... Plt. 82.2

*Primary Examiner*—Howard J. Locker

*Attorney, Agent, or Firm*—Burns, Doane, Swecker & Mathis

[57] ABSTRACT

A new and distinct cultivar of Chrysanthemum plant named Touch is provided. The new cultivar was the result of a controlled breeding program wherein the Dinara variety (non-patented in the United States) was pollinated by the Penny Lane cultivar (U.S. Plant Pat. No. 6,238). More specifically, the new cultivar forms attractive bicolored single anemone flowers wherein the petals are yellow and the disc florets particularly towards the center of the cushion bear a distinctive orange-brown coloration (as illustrated). The inflorescence tends to be of the flat capitulum type when mature. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Touch.

The new cultivar is the product of a planned breeding program which had as its objective the creation of a new Chrysanthemum cultivar which exhibits attractive relatively large single anemone bicolored flowers having yellow ray florets and a distinctive brownish center, a flower response period of approximately eight weeks, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1985 at De Lier, The Netherlands. The female parent (i.e., the seed parent) was the Dinara cultivar (non-patented in the United States) and the male parent (i.e., the pollen parent) was the Penny Lane cultivar (U.S. Plant Pat. No. 6,238). The parentage of the new cultivar can be summarized as follows:

DINARA × PENNY LANE.

The seeds resulting from the above pollination were sown and plantlets were obtained which were physically and biologically different from each other. Selective study during 1986 resulted in the identification of a single plant of the new variety.

It was found that the new cultivar of the present invention:

(a) exhibits attractive single anemone flowers having an overall diameter of approximately 55 to 65 mm., yellow ray florets, and disc florets particualrly towards the center of the cushion which are orange-brown in coloration, (b) bears flowers in a generally flat capitulum configuration when mature, (c) exhibits a flower response period of approximately eight weeks, (d) forms attractive dark green foliage, and (e) has the ability to produce flowers of commercially acceptable quality throughout the year in a cut mum production program.

Asexual reproduction of the new cultivar by cuttings initially taken during 1986, as performed at De Lier, The Netherlands, in a controlled environment has demonstrated that the characteristics of the new cultivar as herein disclosed are firmly fixed and are retained through successive generations of asexual propagation.

Touch has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Improved Hoof Lane cultivar which is similar to the Hoof Lane cultivar (U.S. Plant Pat. No. 6,299), the Touch cultivar is found to exhibit a larger flower size (e.g., an overall diameter of approximately 55 to 65 mm. vs. approximately 50 mm.), a larger flower center (e.g., approximately 23 mm. vs. 17 mm.), smaller and slightly paler green foliage, and reduced tolerance to leaf miner. The vegetative growth, response time, and the low temperature tolerance are substantially identical to the corresponding characteristics of the Improved Hoof Lane cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during April 1991. The plants described were grown under standard greenhouse conditions which approximate those commonly utilized for the production of cut mums.

Classification:

*Botanical.*—*Chrysanthemum morifolium* Ramat., cv. Touch.

*Commercial.*—Cut anemone spray.

INFLORESCENCE

A. Capitulum:

*Form.*—Generally flat when mature.

*Type.*—Anemone.

*Diameter across face.*—Approximately 55 to 65 mm. on average.

*Diameter of flower center.*—Approximately 23 mm. on average.

B. Corolla of ray and disc florets:

*Color (general tonality from a distance of three meters).*—Yellow with dark center.

*Color ray florets.*—(Top surface) — Yellow, Yellow-Orange Group 15A. (under surface) — Ranges from Yellow-Orange Group 15A to Orange-Red Group 31B.

*Color disc florets.*—Yellow with orange-brown coloration at the center of the cushion, Greyed-Orange Group 169A.

C. Reproductive organs:

*Gynoecium.*—Present in ray florets.

PLANT

A. General appearance:

*Height.*—Approximately 100 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Touch substantially as herein shown and described, which:

(a) exhibits attractive single anemone flowers having an overall diameter of approximately 55 to 65 mm., yellow-ray florets, and disc florets particularly towards the center of the cushion which are orange-brown in coloration, (b) bears flowers in a generally flat capitulum configuration when mature, (c) exhibits a flower response period of approximately eight weeks, (d) forms attractive dark green foliage, and (e) has the ability to produce flowers of commercially acceptable quality throughout the year in a cut mum production program.

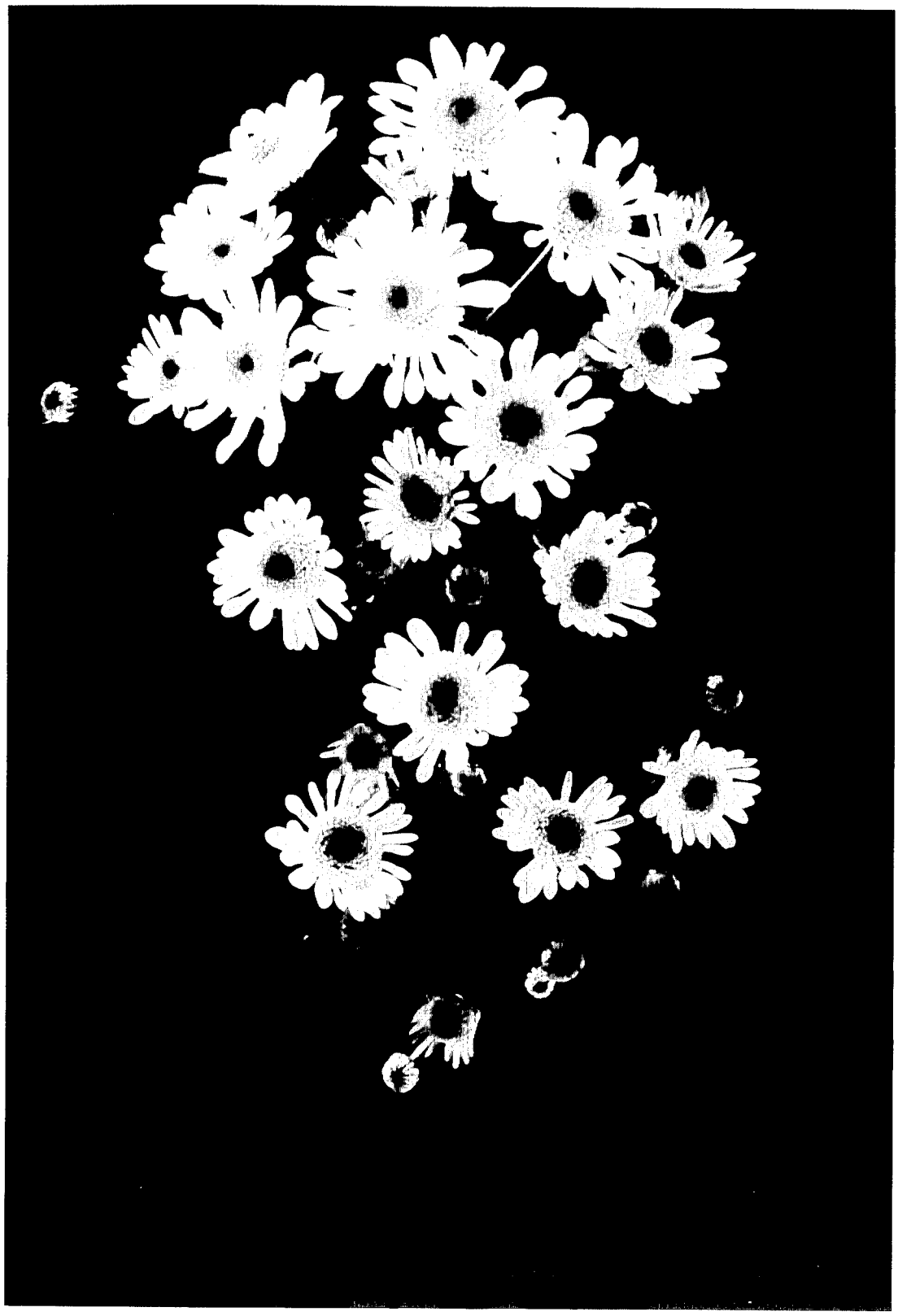

* * * * *